(12) United States Patent
Bolton

(10) Patent No.: US 7,338,537 B2
(45) Date of Patent: Mar. 4, 2008

(54) 2-(AMINO OR SUBSTITUTED AMINO)-3-5-6-SUBSTITUTED PHENOL COMPOUNDS, DYEING COMPOSITIONS CONTAINING THEM, AND USE THEREOF

(75) Inventor: Philip David Bolton, Teddington (GB)

(73) Assignee: The Procter & Gamble Company, Cincinnati, OH (US)

( * ) Notice: Subject to any disclaimer, the term of this patent is extended or adjusted under 35 U.S.C. 154(b) by 236 days.

(21) Appl. No.: 11/204,434

(22) Filed: Aug. 16, 2005

(65) Prior Publication Data

US 2006/0032000 A1  Feb. 16, 2006

(30) Foreign Application Priority Data

Aug. 16, 2004  (EP)  .................. 04254901

(51) Int. Cl.
*A61K 7/13*  (2006.01)

(52) U.S. Cl. .............. 8/405; 8/406; 8/408; 8/410; 8/411; 8/412; 8/416; 8/421; 8/424; 8/435

(58) Field of Classification Search .............. 8/405, 8/406, 408, 410, 411, 412, 416, 421, 424, 8/435

See application file for complete search history.

(56) References Cited

U.S. PATENT DOCUMENTS 4,396,392 A  8/1983  Konrad

FOREIGN PATENT DOCUMENTS

| EP | 0079141 A1 | 5/1983 |
|----|------------|--------|
| EP | 0530166 A2 | 3/1993 |
| WO | WO-93/05012 A1 | 3/1993 |
| WO | WO-02/058654 A1 | 8/2002 |
| WO | WO-02/058657 A1 | 8/2002 |

OTHER PUBLICATIONS

STIC Search Report dated May 30, 2007.*
EP Search Report, Dec. 22, 2005.
Acton, John P. et al, "Nitration, amination, and halogenation of di-O-methylphloracetophenone", *Monatshefte Fuer Chemie*, 113(1), 73-9 Coden: MOCMB7; ISSN: 0026-9247, 1982, XP009042156 compound 7.

Baxter, I. et al, "Reactions between 2,5-di-tert-butyl-1,4-benzoquinone and primary aliphatic amines", *Journal of the Chemical Society*, Perkin Transactions 1: Organic and bio-organic chemistry (1972-1999), (3), 268-72 Coden: JCPRB4; ISSN: 0300-922X, 1973, XP009042160 compound VIA.

Betts, J. J. et al: "Metabolism of the trichloronitrobenzenes in the rabbit", *Biochem. J.*, 66, 610-21, 1957, XP009042270 p. 616, compound 2-amino-3:5:6-trichlorophenol).

Branchini, Rosanna et al: "Some derivatives of p-orsellinic acid" *Annali Di Chimica* (Rome, Italy), 48, 819-25 Coden: ANCRAI; ISSN: 0003-4592, 1958, XP009042172 compounds VII, VIII.

Gerecke, M. et al: "Griseofulvin. IV. Synthesis of griseofulvin analogs" *Helvetica Chimica Acta*, 45, 2241-56 Coden: HCACAV; ISSN: 0018-019X, 1962, XP009042202 compound IIIi.

Kato, Shiro et al: "Synthesis and biological activity of 4-amino-5-chloro-2-ethoxy-3-hydroxybenzamides, metabolites of a new gastroprokinetic agent, mosapride", *Chemical & Pharmaceutical Bulletin*, 44(8), 1484-1492 Coden: CPBTAL; ISSN: 0009-2363, 1996, XP009042205 compounds 3, 4, 22, 36, 40.

Kato, S.: "Synthesis of 4-chloro-7-ethoxy-2(3H)-benzoxazolone-6-carboxylic Acid", *J. Heterocyclic Chem.*, vol. 33, 1996, pp. 1171-1178, XP002312780 compound 6.

Linderberg, Mats et al: "Synthesis and QSAR of substituted 3-hydroxyanthranilic acid derivatives as inhibitors of 3-hydroxyanthranilic acid dioxygenase (3-HAO)", *European Journal of Medicinal Chemistry*, 34(9), 729-744 Coden: EJMCA5; ISSN: 0223-5234, 1999, XP002312779 compounds 6, 8-12.

Pearce, Dan S. et al: "Chemistry of azidoquinones and related compounds. XIV. Thermal rearrangements of 2-azido- and 2,3-diazido-1, 4-quinol diacetates", *Journal of Organic Chemistry*, 39(10), 1362-8 Coden: JOCEAH; ISSN: 0022-3263, 1974, XP002312781 compound 14.

Treibs, Wilhelm et al: "The dihydroxycymenes. IV. Isocymorcin (3,5-dihydroxycymene) from 3,5-methanedione by dehydrogenation and total synthesis", *Journal Fuer Praktische Chemie (Leipzig)*, 13, 291-305 Coden: JPCEAO; ISSN: 0021-8383, 1961, XP009042267 compound VIII.

* cited by examiner

*Primary Examiner*—Eisa Elhilo
(74) *Attorney, Agent, or Firm*—Melissa G. Krasovec

(57) ABSTRACT

The present invention relates to 2-(amino or substituted amino)-3,5,6-substituted phenol compounds according to the Formula (I), as defined herein and compositions for the oxidative dyeing of keratin fibers, comprising a medium suitable for dyeing and a compound of the Formula (I).

10 Claims, No Drawings

2-(AMINO OR SUBSTITUTED AMINO)-3-5-6-SUBSTITUTED PHENOL COMPOUNDS, DYEING COMPOSITIONS CONTAINING THEM, AND USE THEREOF

FIELD OF THE INVENTION

The present invention relates to 2-(amino or substituted amino)-3,5,6-substituted phenol compounds, compositions for the oxidative dyeing of keratin fibres (preferably hair) comprising such compounds, and the use thereof.

BACKGROUND OF THE INVENTION

Dyeing of keratin fibres, particularly hair, is known. The desire to alter the colour of hair is not a facet of modern times. Hair colour is altered to accommodate changes in fashion, style, and personal preference. However, obtaining good colouring and wearability without undesirable side effects to the hair and skin, remains an elusive goal. A suitable method of colouring hair is through oxidative dyeing. A variety of colours may be obtained, including yellows. Although the inventors choose not to speculate on the veracity of the adage according to which reputedly "blondes have more fun," they do recognize that yellow dyes themselves are desired.

Yellow dyes, particularly those used in colouring hair, should provide good colouring, including intensity of colouration and/or fastness, and be able to perform in spite of external agents, such as light, particularly sunlight, adverse weather conditions, washing and styling, permanent waving, perspiration, and/or friction. Such dyes should also be favourable as to toxicology and dermatology. They should be useful in providing a wide range of shades when combined with other ingredients and process stages, too.

The use of 2-aminophenol (also known as ortho-aminophenol or OAP) and some derivatives thereof, for yellow dyeing of keratin typically achieved by self coupling is known. For example, U.S. Pat. No. 4,396,392 (Wella, AG) discloses 2-amino-5-methyl-phenol and WO 02/058,657 (Clairol, Inc.) discloses 2-(amino or amino substituted)-5-methyl-phenol each for use in providing yellow colour, alone and in combination with other colouring agents.

However, many previous oxidative dye compounds and combinations of such compounds resulting in yellow colourations have demonstrated poor wearability and stability to light, and some have recently experienced objections to their use from a toxicological standpoint. OAP, in particular, has been found to provide poor yellow, e.g. with off-tones. One alternative approach has been to use direct non-oxidative dyes alone or in combination with lessened quantities of oxidative dyes. However, this approach has been found to result in poor wash fastness upon shampooing, among other undesirable effects. Thus, there remains a need to provide further oxidative dye alternatives to known dyes, preferably yellow dyes, and compositions for dyeing of hair comprising them, that produce good colouration, preferably a bright yellow colouration, that exhibit good dye uptake by the hair, are useful in providing shades or colours which are stable over a reasonable period of time, provide good wash fastness and wearability, good selectivity, do not undergo significant change on exposure to light, shampooing or acid perspiration, and/or exhibit a favourable safety profile.

It has now been surprisingly found that by placing specific substituents in the 3,5 and 6 position of 2-amino and 2-(substituted amino) phenols, compounds exhibiting one or more of the aforementioned desirable qualities may be provided. Without being bound by theory, it is believed that the addition of such substituents in these positions may provide similar improved yellow colour formation and wash fastness with improved toxicology via steric hinderance of the active groups (—OH, $NH_2$) versus previous 2-amino phenols and 2-amino phenol derivatives.

Similar compounds have been described for example in EP530166 which describes 3-hydroxy anthranilic acid derivatives for inhibiting 3-hydroxy anthranilate oxygenase and EP079141 which describes aminoresorcinol derivatives which have inhibitory activity on 5-lipoxygenase.

SUMMARY OF THE INVENTION

The present invention relates to 2-(amino or substituted amino)-3,5,6-substituted phenol compounds according to the Formula (I), as defined herein. The substituents may themselves be substituted or unsubstituted. This invention further relates to a composition for the oxidative dyeing of keratin fibres, comprising a medium suitable for dyeing and a compound of the Formula (I), as defined herein. This invention further relates to a method for oxidative dyeing of keratin fibres, comprising applying such compositions in the presence of an oxidizing agent, for a period sufficient to develop the desired colouration.

DETAILED DESCRIPTION OF THE INVENTION

Except as otherwise noted, amounts represent approximate weight percent of the actual amount of the ingredient, and do not include solvents, fillers or other materials which may be combined with the ingredient in commercially available products, and the amounts include the composition in the form of intended use. Except as otherwise noted, all amounts including part, percentages, and proportions are understood to be modified by the word "about", and amounts are not intended to indicate significant digits.

As used herein, the term "hair" refers to keratinous fibres on a living, e.g. a person, or non-living body, e.g. in a wig, hairpiece, or other aggregation of non-living keratinous fibres. Mammalian, preferably human, hair is preferred. Notably, hair, wool, fur, and other keratinous fibres are suitable substrates for colouring by the compounds and compositions described herein.

As used herein, the term "hair dyeing composition" refers to the composition containing one or more oxidation dyes, including the compounds described herein, prior to admixture with the developer composition. The term "developer composition" (which encompasses the term oxidizing agent composition) refers to compositions containing an oxidizing agent prior to admixture with the hair dyeing composition. The term "hair dyeing system" refers to the combination of the hair dyeing composition and the developer composition before admixture, and may further include a conditioner product and instructions, such product or system often being provided packaged as a kit. The term "hair dyeing product composition" refers to the composition formed by mixing the hair dyeing composition and the developer composition.

As used herein, "heteroalkyl" means a paraffinic (paraffin is also called alkane) hydrocarbon group containing at least one heteroatom (element other than carbon).

As used herein, "heteroaliphatic" means a group of organic compounds characterised by straight- or branched-chain arrangement of the constituent carbon comprising at least one heteroatom. Heteroaliphatics are comprised of three sub-groups: heteroalkanes, all of which are saturated;

heteroalkenes, which are unsaturated; and heteroalkynes, which contain a triple bond. In complex structures the chains may be branched or cross-linked.

As used herein, "heteroolefinic" means a class of unsaturated hydrocarbons containing at least one heteroatom and having one of more double bonds. Those containing one double bond are called heteroalkenes, and those with two heteroalkadienes, or heterodiolefin. They are named after their corresponding paraffins by adding '-ene' or '-ylene' to the stem.

As used herein, "cosmetically acceptable" means that ingredients which the term describes are suitable for use in contact with the skin or hair of humans and lower animals without undue toxicity, incompatibility, instability, irritation, allergic response, and the like.

I. Compounds

The inventive compounds are compounds of the Formula (I), or its salts with an inorganic or organic acid:

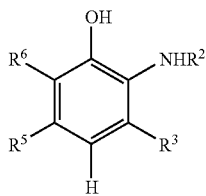

(I)

wherein $R^3$, $R^5$ and $R^6$ are substituted $R^4$ is not substituted and is H and wherein $R^3$, $R^5$ and $R^6$ are independently selected from:

(a) the group of C-linked preferably monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) independently comprising from 1 to 10 carbon atoms and from 0 to 5 heteroatoms independently selected from O, S, N, P, and Si;

(b) the group of S-linked, preferably monovalent, substituents consisting of $SA^{16}$, SCN, $SO_2A^{16}$, $SO_3A^{16}$, $SSA^{16}$, $SOA^{16}$, $SO_2NA^{16}A^{17}$, $SNA^{16}A^{17}$, and $SONA^{16}A^{17}$;

(c) the group of O-linked, preferably monovalent, substituents, consisting of $OA^{19}$, OCN and $ONA^{16}A^{17}$;

(d) the group of N-linked, preferably monovalent, substituents, consisting of $NA^{16}A^{20}$, $(NA^{16}A^{17}A^{18})^+$, NC, $NA^{16}OA^{17}$, $NA^{16}SA^{17}$, NCO, NCS, $N=NA^{16}$, $N=NOA^{16}$, $NA^{16}CN$, $NA^{16}NA^{17}A^{18}$;

(e) the group of preferably monovalent, substituents, consisting of $COOA^{19}$, $CON_3$, $CONA^{16}_2$, $CONA^{16}COA^{17}$, $C(=NA^{16})NA^{16}A^{17}$, CHO, CHS, CN and NC, and (f) the group consisting of fluoroalkyl monovalent substituents consisting of mono-, poly-, or per-fluoro alkyl systems comprising from 1 to 12 carbon atoms and from 0 to 4 heteroatoms.

Preferably $R^3$, $R^5$ and $R^6$ are independently selected from:

(a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) independently comprising from 1 to 10 carbon atoms and from 0 to 5 independently heteroatoms selected from O, S and N, (e) the group of monovalent substituents consisting of $COOA^{19}$, $CON_3$, $CONA^{16}_2$, $CONA^{16}COA^{17}$, $C(=NA^{16})NA^{16}A^{17}$, CHO, CHS, CN and NC, and (f) the group consisting fluoroalkyl monovalent substituents consisting of mono-, poly-, or per-fluoro alkyl systems comprising from 1 to 8 carbon atoms and from 0 to 3 heteroatoms.

More preferably $R^3$, $R^5$ and $R^6$ are independently selected from:

(a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) independently comprising from 1 to 6 carbon atoms and from 0 to 2 heteroatoms independently selected from O, S and N.

Most preferably $R^3$, $R^5$ and $R^6$ are independently selected from:

(a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems comprising from 1 to 6 carbon atoms and from 0 to 2 heteroatoms selected from O, S and N.

For the groups (b) to (e), described hereinabove, $A^{16}$, $A^{17}$, and $A^{18}$ are monovalent and are independently selected from:

(1) H, (2) substituted or unsubstituted, straight or branched, alkyl, mono- or poly-unsaturated alkyl, heteroalkyl, aliphatic, heteroaliphatic, or heteroolefinic systems, (3) substituted or unsubstituted, mono- or poly-cyclic aliphatic, aryl, or heterocyclic systems, or (4) substituted or unsubstituted, mono-, poly-, or per-fluoro alkyl systems; said systems of (2), (3) and (4) comprising independently from 1 to 10 carbon atoms and from 0 to 5 heteroatoms independently selected from O, S, N, P, and Si.

$A^{19}$ is monovalent and independently selected from (1) substituted or unsubstituted, straight or branched, alkyl, mono- or poly-unsaturated alkyl, heteroalkyl, aliphatic, heteroaliphatic or heteroolefinic systems, (2) substituted or unsubstituted, mono or poly-cyclic aliphatic, aryl, or heterocyclic systems, or (3) substituted or unsubstituted, mono-, poly- or per-fluoro alkyl systems;

said system (1) comprises from 3 to 10 carbon atoms and from 0 to 5 heteroatoms and said systems of (2) and (3) comprising independently from 2 to 10 carbon atoms and from 0 to 5 heteroatoms independently selected from O, S, N, P and Si.

$A^{20}$ is monovalent and is independently selected from:

(1) substituted or unsubstituted, straight or branched, alkyl, mono- or poly-unsaturated alkyl, heteroalkyl, aliphatic, heteroaliphatic, or heteroolefinic systems, (2) substituted or unsubstituted, mono- or poly-cyclic aliphatic, aryl, or heterocyclic systems, or (3) substituted or unsubstituted, mono-, poly-, or perfluoro alkyl systems; said systems of (1), (2) and (3) independently comprising from 1 to 10 carbon atoms and from 0 to 5 heteroatoms independently selected from O, S, N, P, and Si.

$R^2$ may be selected from any of the groups described for $R^3$, $R^5$ and $R^6$ hereinabove namely (a), (b), (c), (d), (e), (f) and hydrogen. Preferably $R^2$ is selected from the groups (a), (b) (c) and H, and most preferably $R^2$ is hydrogen.

Particularly preferred compounds of the present invention are listed below, wherein $R^3$, $R^5$ and $R^6$ are independently selected from methyl, ethyl and —CH$_2$—O—CH$_3$ and $R^2$ is H:

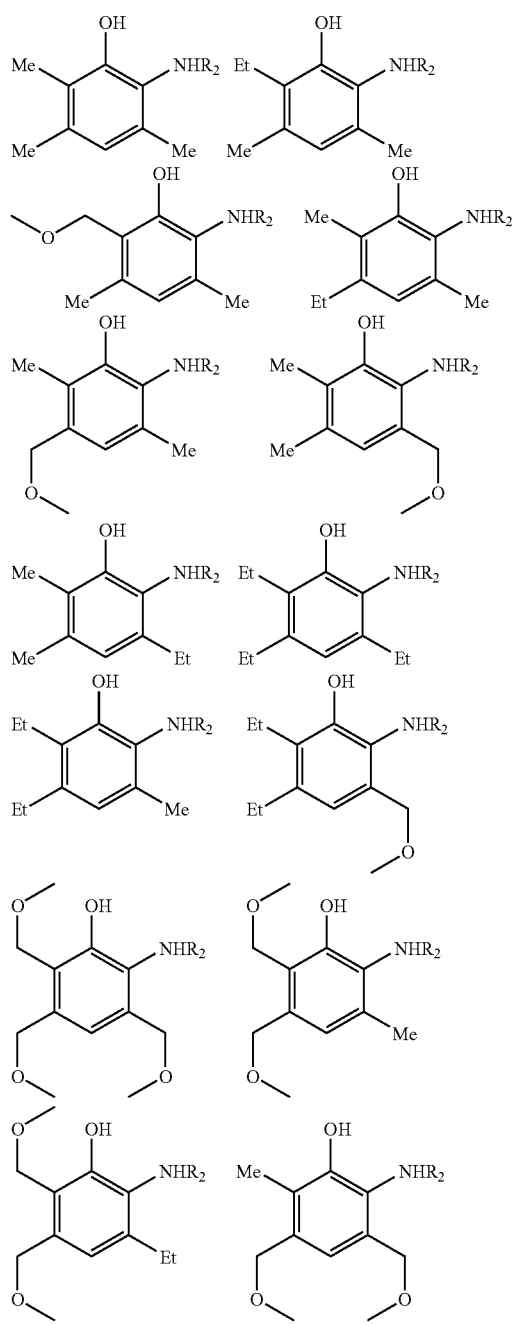

-continued

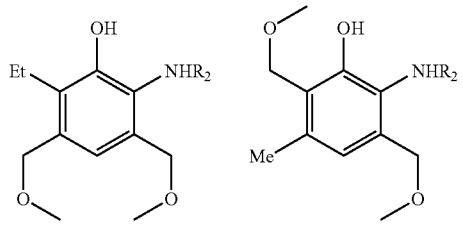
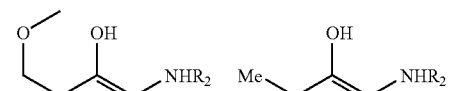
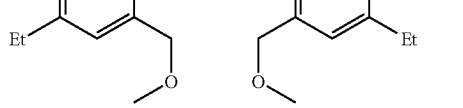
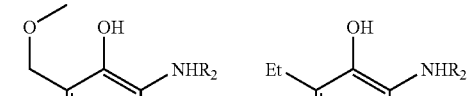
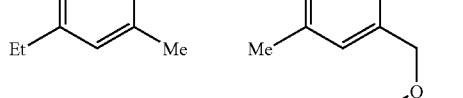
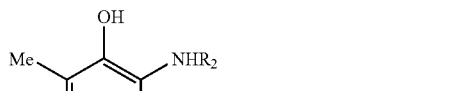
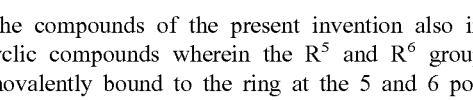
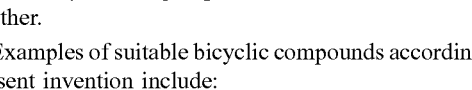
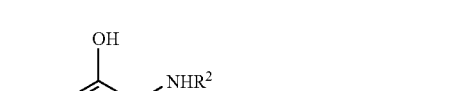

The compounds of the present invention also include bicyclic compounds wherein the $R^5$ and $R^6$ groups are monovalently bound to the ring at the 5 and 6 positions respectively and the groups $R^5$ and $R^6$ are also bonded to one another.

Examples of suitable bicyclic compounds according to the present invention include:

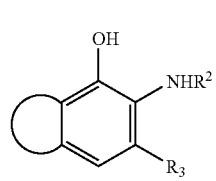

where the additional ring is a 5- or 6-membered, carbocyclic or heterocyclic ring with or without further substitutions.

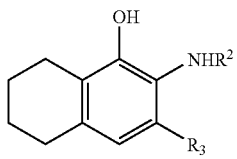

wherein $R_3$=methyl, ethyl and —$CH_2$—O—$CH_3$

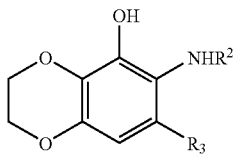

$R_3$=methyl, ethyl and —$CH_2$—O—$CH_3$

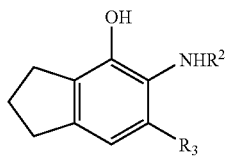

$R_3$=methyl, ethyl and —$CH_2$—O—$CH_3$

The 3,5,6 substituted amino phenols of the present invention may be readily synthesised using routes known in the literature. The most common route to 2-aminophenols is by the nitration of the phenol with dilute aqueous nitric acid, followed by reduction of the readily separated 2-nitro isomer to 2-aminophenol. The most common and general route to the polysubstituted 2-aminophenols is the same, but starting from the appropriately substituted phenol. Thus the 3,5,6-trisubstituted 2-aminophenols require the appropriately substituted tri-substituted phenol, as shown; 2,3,5-tri-subs$^d$ phenol

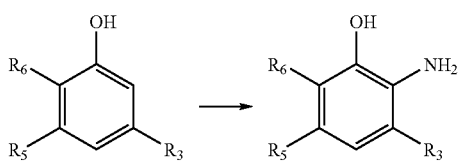

3,5,6-di-subs$^d$ 2-aminophenol

The $R^3$, $R^5$ and $R^6$ groups in each case can be the same or different as defined herein above.

The following generic classes are readily synthesized in order to produce the required starting materials.

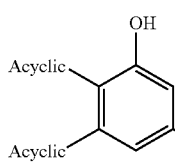 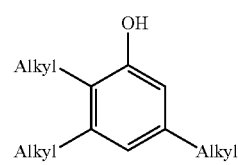

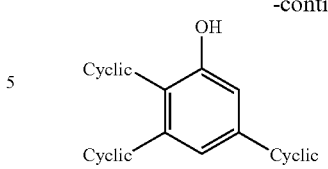

-continued

Moreover, a number of the starting compounds are also commercially available (e.g. from Aldrich), as listed below, whilst many more compounds could be readily synthesised using the standard methods described hereinabove.

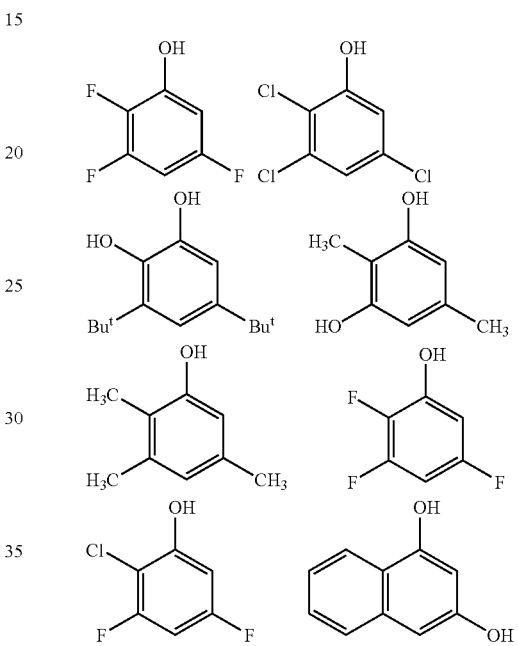

Whilst the general route to these compounds, described above, is based on phenols as the starting materials, in particular cases it may be more attractive to introduce the phenolic group during the synthesis. The main methods available for this route are summarized below;

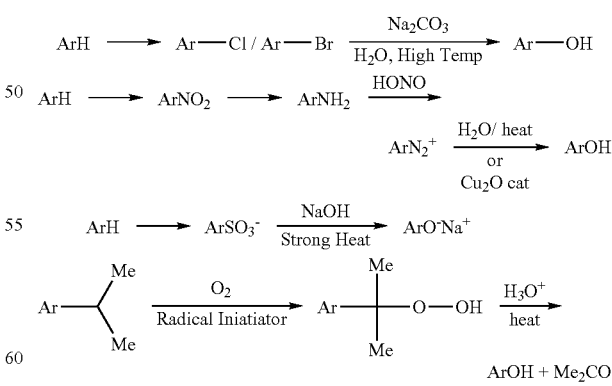

For several other routes see 'Comprehesive Organic Functional Group Transformations', Elsevier, Vol. 2 pp. 646-674.

As phenols are electron rich they are very reactive towards electrophilic substitution, as in the nitration reactions above. Consequently, other standard electrophilic aromatic substitution reactions, such as halogenation, sulphonation, alkylation and acylation are thus also applicable. Additionally, there is a group of reactions specific to phenols which are available for the introduction of substituents such as those illustrated below;

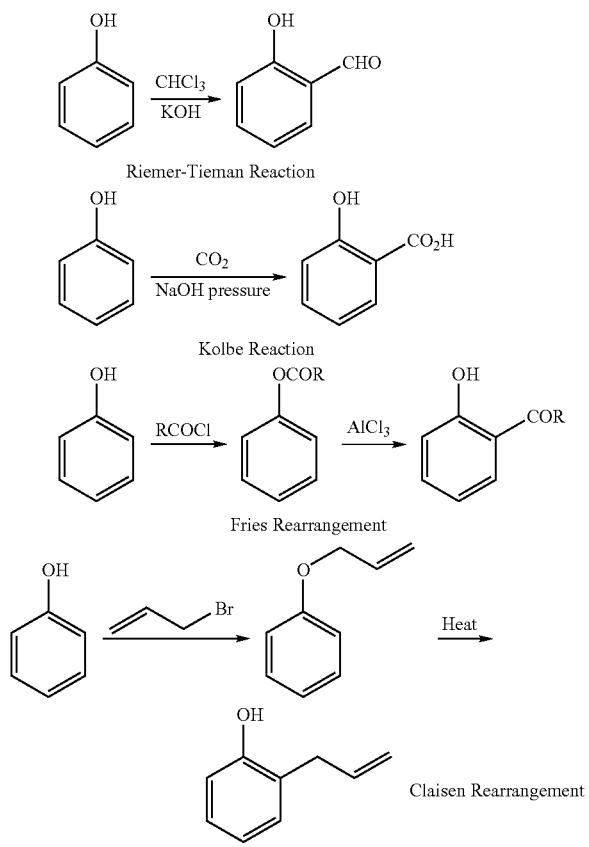

An alternative route is to utilize the re-arrangement of N-aryl-hydroxylamines into o-aminophenols (if the p position is blocked) as illustrated below:

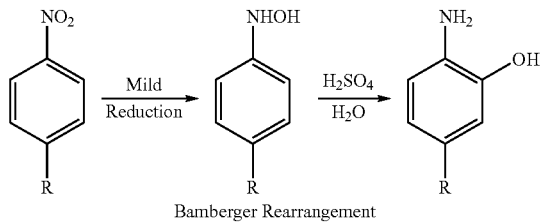

ARNHOH can also be formed by careful oxidation of ArNH$_2$. The potentially valuable aspect of this rearrangement for this synthesis is that in all cases the position para to the NHOH is blocked (hence the usually major isomer cannot be formed), thus there is only one ortho position for introduction of the OH group. This is an advantage over the nitration and reduction of the phenol route.

Given that the OH and NH$_2$ groups of aminophenols are reactive, it may be necessary in some synthetic sequences to 'protect' one or both of them to avoid unwanted chemistry. This is readily done for OH by alkylation (e.g. methylation) and deblocking with acid (HBr), and for NH$_2$ by acylation (e.g. acetylation) and deblocking with base (aq. NaOH);

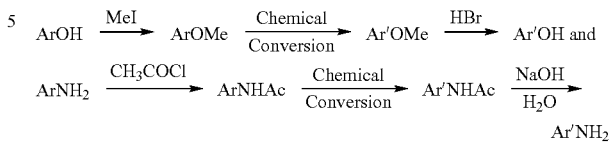

Alternatively, both functional groups can be protected at the same time if necessary by forming them into a cyclic structure, for example;

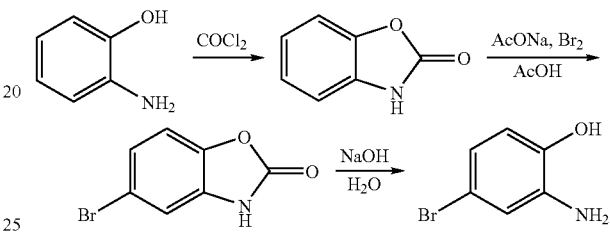

Finally, in electrophilic substitution of the aromatic ring in a given synthesis, the most reactive site of substitution may not be the desired one. In such cases, the most reactive site may be sulphonated (with H$_2$SO$_4$ or SO$_3$/H$_2$SO$_4$) thereby blocking this position. Electrophilic substitution at the desired site is then followed by deblocking the sulphonic acid by heating with dilute sulphuric acid (since sulphonation is a reversible reaction). For example (the main product being the para-substituted compound due to steric reasons);

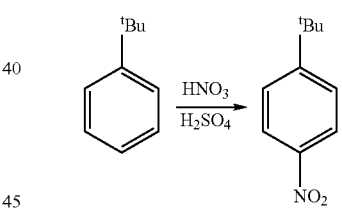

However, the ortho-isomer may also be prepared as follows;

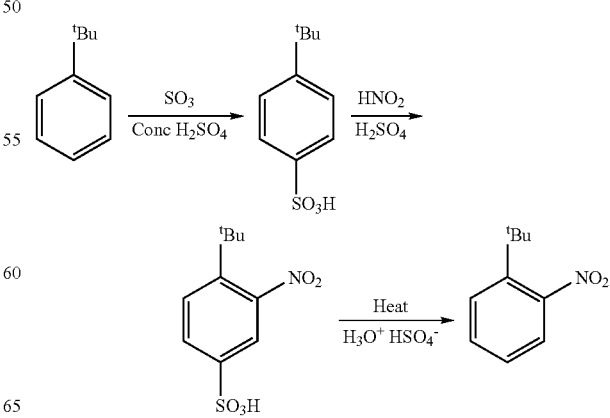

Thus, by using the chemistry summarized herein above, it is possible to prepare the desired 3,5,6 substituted 2-(amino or substituted amino) phenol of the present invention.

II. Composition Components

The inventive invention further relates to compositions for the oxidative dyeing of keratin fibres comprise a medium suitable for dyeing and a compound of the Formula (I), or its salts with an inorganic or organic acid. Such compounds will typically be present in an amount ranging from 0.001% to 10%, preferably from 0.01% to 5%, by weight, of the hair dye composition.

The medium suitable for dyeing may be selected from water, or a mixture of water and at least one organic solvent to dissolve the compounds that would not typically be sufficiently soluble in water. Suitable organic solvents for use herein include, but are not limited to: C1 to C4 lower alkanols (e.g., ethanol, propanol, isopropanol), aromatic alcohols (e.g. benzyl alcohol and phenoxyethanol); polyols and polyol ethers (e.g., carbitols, 2-butoxyethanol, propylene glycol, propylene glycol monomethyl ether, diethylene glycol monoethyl ether, monomethyl ether, hexylene glycol, glycerol, ethoxy glycol), and propylene carbonate. When present, organic solvents are typically present in an amount ranging from 1% to 30%, by weight, of the composition. Preferred solvents are water, ethanol, propanol, isopropanol, glycerol, 1,2-propylene glycol, hexylene glycol, ethoxy diglycol, and mixtures thereof.

The inventive compositions may, in some embodiments, further comprise additional optional components known, conventionally used, or otherwise effective for use in oxidative dye compositions, including but limited to: primary intermediate dye compounds; coupler dye compounds; direct dyes; anionic, cationic, nonionic, amphoteric or zwitterionic surfactants, or mixtures thereof; anionic, cationic, nonionic, amphoteric or zwitterionic polymers, or mixtures thereof; inorganic or organic thickeners; conditioning agents; oxidising agents; alkalising agents; antioxidants and radical scavengers; penetration agents; chelating and sequestering agents; fragrances; buffers; dispersing agents; peroxide stabilizing agents; natural ingredients, e.g. proteins and protein derivatives, and plant materials (e.g. aloe, chamomile and henna extracts); silicones (volatile or non-volatile, modified or non-modified), film-forming agents, ceramides, preserving agents; and opacifiers.

Some adjuvants referred to above, but not specifically described below, which are suitable are listed in the International Cosmetics Ingredient Dictionary and Handbook, ($8^{th}$ ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

Oxidative Dye Compounds

The oxidative dye precursors according to Formula I (above) that are comprised within the inventive compositions may be present alone as dyeing agents, and can advantageously behave both like an oxidation base and like a coupler, e.g. self-coupling compounds. They may also be used in combination with one or more primary intermediates, and/or couplers, and in combination with one or more oxidizing agent. All known coupler and primary intermediate combinations are usable in the inventive compositions.

The compounds suitable for use in the inventive compositions (including those optionally added), in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic OH groups, in the form of their salts with bases, such as alkali phenolates.

Optional couplers, when present, are typically present in an amount such that in aggregate the concentration of couplers and the compounds of Formula (I) in the composition ranges from 0.002% to 10%, preferably from 0.01% to 5%, by weight, of the hair dyeing composition. Optional primary intermediates, when present, are present in an effective dyeing concentration, typically an amount from 0.001% to 10%, preferably from 0.01% to 5%, by weight, of the hair dyeing composition. The total amount of dye compounds (e.g., optional primary intermediates, optional coupler compounds, and the compounds of Formula (I)) in the hair dyeing compositions of this invention will typically range from 0.002% to 20%, preferably from 0.04% to 10%, more preferably from 0.1% to 7%, by weight, of the hair dyeing composition.

Primary Intermediates

Suitable primary intermediates for use in the compositions described herein include, but are not limited to p-phenylenediamine derivatives, e.g. benzene-1,4-diamine (commonly known as p-phenylenediamine), 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (commonly known as N,N-bis(2-hydroxyethyl)-p-phenylenediamine) (2,5-diamino-phenyl)-methanol, 1-(2'-Hydroxyethyl)-2,5-diaminobenzene, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino] butyl}benzene-1,4-diamine, and 2-[2-(2-{2-[(2,5-diaminophenyl)-oxy]ethoxy}ethoxy)ethoxy]benzene-1,4-diamine; 1,3-Bis(N(2-Hydroxyethyl)-N-(4-amino-phenyl) amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylinediamine;

p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-1-hydroxy-2-(2'-hydroxyethylaminomethyl)benzene, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)-phenol, 4-amino-2-fluoro-phenol; 1-Hydroxy-2,4-diaminobenzene; 1-(2'-Hydroxyethyloxy)-2,4-diaminobenzene; 2,4-Diamino-5-methylphenetol;

o-phenylenediamine derivatives such as: 3,4-Diaminobenzoic acid and salts thereof;

o-aminophenol derivatives such as: 2-amino-phenol (commonly known as o-aminophenol), 2,4-diaminophenol, 2-amino-5-methyl-phenol, 2-amino-6-methyl-phenol, N-(4-amino-3-hydroxy-phenyl)-acetamide, 2-amino-4-methyl-phenol, 2-amino-5-ethyl-phenol, 2-amino-5-phenyl phenol and 2-amino-5-methoxymethyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1 H-pyrazole-4,5-diamine, 1-(4-chlorobenzyl)-1H-pyrazole-4,5-diamine, pyrazolo[1,5-a]-pyrimidine-3,7-diamine, 5,6,7-trimethylpyrazolo[1,5-a]pyrimidin-3-ylamine hydrochloride, 7-methylpyrazolo[1,5-a]pyrimidin-3-ylamine hydrochloride, 2,5,6,7-teramethyl-pyrazolo[1,5-a]pyrimidin-3-ylamine hydrochloride, 5,7-di-tert-butylpyrazolo[1,5-a]pyrimidin-3-ylamine hydrochloride, 5,7-di-trifluoromethyl-pyrazolo[1,5-a]pyrimidin-3-ylamine hydrochloride, 2-methylpyrazolo[1,5-a]pyrimidin-3,7-diamine hydrochloride; 4-Hydroxy-2,5,6-triaminopyrimidine; 1-(2'hydroxyethyl)-amino-3,4-methylene dioxybenzene; and 1-Hydroxyethyl-4,5-diaminopyrazole sulphate.

Preferred primary intermediates include but are not limited to: p-phenylenediamine derivatives such as: 2-methyl-benzene-1,4-diamine; benzene-1,4-diamine; 1-(2,5-diamino-phenyl)-ethanol; 2-(2,5-diamino-phenyl)-ethanol; N-(2-methoxyethyl)benzene-1,4-diamine; 2-[(4-amino-phenyl)-(2-hydroxy-ethyl)-amino]-ethanol; 1-(2,5-diaminophenyl)ethane-1,2-diol; 1-(2'-Hydroxyethyl)-2,5-diaminobenzene; 1,3-Bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylinediamine; and mixtures thereof;

p-aminophenol derivatives such as: 4-amino-phenol, 4-methylamino-phenol, 4-amino-3-methyl-phenol, 4-amino-2-methoxymethyl-phenol; 1-(5-amino-2-hydroxy-phenyl)-ethane-1,2-diol; 1-Hydroxy-2,4-diaminobenzene; 1-(2'-Hydroxyethyloxy)-2,4-diaminobenzene; 4-Amino-2-aminomethylphenol; 2,4-Diamino-5-methylphenetol; 4-Amino-1-hydroxy-2-(2'-hydroxyethylaminomethyl)benzene; 1-methoxy-2-amino-4-(2'hydroxyethylamino)benzene; 5-aminosalicylic acid and salts thereof; and mixtures thereof;

o-phenylenediamine derivatives such as: 3,4-Diaminobenzoic acid and salts thereof;

o-aminophenol derivatives such as: 2-amino-phenol, 2-amino-5-methyl-phenol, 2-amino-6-methyl-phenol, N-(4-amino-3-hydroxy-phenyl)-acetamide; 2-amino-4-methyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-dimethyl-pyridine-2,5-diamine; 4-Hydroxy-2,5,6-triaminopyrimidine; 1-(2'hydroxyethyl)-amino-3,4-methylene dioxybenzene; and 1-Hydroxyethyl-4,5-diaminopyrazole sulphate; and mixtures thereof.

More preferred primary intermediates include: 2-methyl-benzene-1,4-diamine; benzene-1,4-diamine; N,N-Bis(2-hydroxyethyl)-p-phenylinediamine; 4-amino-phenol; 4-methylamino-phenol; 4-amino-3-methyl-phenol; 1-Hydroxy-2,4-diaminobenzene; 2-amino-phenol; 2-amino-5-methyl-phenol; 2-amino-6-methyl-phenol; 1-methyl-1H-pyrazole-4,5-diamine; 1-Hydroxyethyl-4,5-diaminopyrazole sulphate; 2-(4,5-diamino-1H-pyrazol-1-yl)ethanol; and mixtures thereof.

Couplers

Suitable couplers for use in the compositions described herein include, but are not limited to: phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, 2,3-dihydroxy-[1,4]naphthoquinone; and 1-Acetoxy-2-methylnaphthalene;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methyl-benzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, 2,4-Diamino-5-(2'-hydroxyethyloxy)toluene; N,N-Dimethyl-3-ureidoaniline; N-(2-aminoethyl)benzene-1,3-diamine, 4-{[(2,4-diaminophenyl)oxy]methoxy}-benzene-1,3-diamine, 1-methyl-2,6-bis(2-hydroxyethylamino)benzene; and 2,4-dimethoxybenzene-1,3-diamine;

m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenyl, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxy-propyl)amino]-2- methylphenol, 3-[(3-hydroxy-2-methylphenyl)-amino]propane-1,2-diol, 3-[(2-hydroxyethyl)amino]-2-methylphenol; 1-Methyl-2-hydroxy-4-(2'-hydroxyethyl)amino-benzene; 1,3-Bis-(2,4-Diaminophenoxy)propane; 1-Hydroxy-2-methyl-5-amino-6-chlorobenzene; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxy-ethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine; 3,4-dihydro-2H-1,4-benzoxazin-6-amine; 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, 2,6-dihydroxypyridine, 2,6-dihydroxy-3,4-dimethylpyridine, 5-methylpyrazolo[5,1-e]-1,2,3-triazole, 5-methyl-6-chloropyrazolo[5,1-e]-1,2,3,-triazole, 5-phenylpyrazolo[5,1-e]-1,2,3-triazole and its addition salts, 1H-2,6-dimethylpyrazolo[1,5-b]-1,2,4-triazole tosylate, 7,8-dicyano-4-methylimidazolo-[3,2-a]imidazole, 2,7-dimethylpyrazolo[1,5-a]pyrimidin-5-one, 2,5-dimethylpyrazolo[1,5-a]pyrimidin-7-one, and 2-methyl-5-methoxymethyl-pyrazolo[1,5-a]pyrimidin-7-one; 6-Hydroxybenzomorpholine; and 3-Amino-2-methylamino-6-methoxypyridine; 1-Phenyl-3-methyl-5-pyrazolone-2,4-dihydro-5,2-phenyl-3H-pyrazole-3-one.

Preferred couplers include but are not limited to: phenol, resorcinol, and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol; 1,2,4-Trihydroxybenzene; 1-Acetoxy-2-methylnaphthalene;and mixtures thereof;

m-phenylenediamine derivatives such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diaminophenoxy)-propan-1-ol; 2,4-Diamino-5-(2'-hydroxyethyloxy)toluene; N,N-Dimethyl-3-ureidoaniline; 2,4-Diamino-5-fluorotoluenesulfatehydrate; 1-methyl-2,6-bis(2-hydroxyethylamino)benzene; and mixtures thereof;

m-aminophenol derivatives such as: 3-amino-phenol, 5-amino-2-methyl-phenol, 5-(2-hydroxy-ethylamino)-2-methyl-phenol, and 3-amino-2-methyl-phenol; 1-Methyl-2-hydroxy-4-(2'-hydroxyethyl)aminobenzene; 1-Hydroxy-3-amino-2,4-dichlorobenzene; 1,3-Bis-(2,4-Diaminophenoxy)propane; 1-Hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, 2-aminopyridin-3-ol, 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, 2,6-dihydroxypyridine; 2,6-dihydroxy-3,4-dimethylpyridine; 6-Hydroxybenzomorpholine; 2,6-Dihydroxy-3,4-dimethylpyridine; 3,5-Diamino-2,6-dimethoxypyridine; 3-Amino-2-methylamino-6-methoxypyridine; 1-Phenyl-3-methyl-5-pyrazolone-2,4-dihydro-5,2-phenyl-3H-pyrazole-3-one; and mixtures thereof.

More preferred couplers include: benzene-1,3-diol; 4-chlorobenzene-1,3-diol; 2-methyl-benzene-1,3-diol; benzene-1,3-diamine; 3-amino-phenol; 5-amino-2-methyl-phenol; 1-Methyl-2-hydroxy-4-(2'-hydroxyethyl)aminobenzene; 4-methyl-2-phenyl-2,4-dihydro-3H-pyrazol-3-one; 2-aminopyridin-3-ol; 1-phenyl-3-methylpyrazol-5-one; 1-Phenyl-3-methyl-5-pyrazolone-2,4-dihydro-5,2-phenyl-3H-pyrazole-3-one; and mixtures thereof.

Primary Intermediate-Coupler Combinations

Preferred primary intermediate and coupler combinations include, but are not limited to: (a) resorcinol, 4-amino-m-cresol, 2-methylresorcinol, 4-amino-2-hydroxytoluene, m-aminophenol and 2-amino-4-hydroxyethyl anisole sulphate; (b) resorcinol, 4-Amino-m-cresol, 2-methyl-resorcinol, 4-amino-2-hydroxytoluene, m-aminophenol, 2-amino-4-hydroxyethyl anisole sulphate, 1-napthol and toluene-2,5-diamine; (c) 2-methyl-5-hydroxyethylaminophenol, resorcinol, toluene-2,5-diamine, m-aminophenol, p-aminophenol and p-methylaminophenol; (d) 2-methyl-5-hydroxyethylaminophenol, m-aminophenol, p-aminophenol, p-methylaminophenol and p-phenylenediamine; (e) 1-hydroxyethyl-4,5-diamino pyrazole sulphate and m-aminophenol; and (f) 2-methylresorcinol, p-aminophenol, 4-amino-2-hydroxytoluene, p-phenylenediamine and N,N-Bis(2-hydroxyethyl)-p-phenylenediamine.

Direct Dyes

The inventive compositions may also comprise compatible direct dyes, in an amount sufficient to provide additional colouring, particularly with regard to intensity. Typically, such an amount will range from 0.05% to 4%, by weight, of the composition. Suitable direct dyes include but are not limited to: Acid Yellow 1, Acid Orange 3, Disperse Red 17, Basic Brown 17, Acid Black 52, Acid Black 1, Disperse Violet 4,4-Nitro-o-Phenylenediamine, 2-Nitro-p-Phenylenediamine, Picramic Acid, HC Red No. 13, 1,4-Bis-(2'-Hydroxyethyl)-amino-2-nitrobenzene, HC Yellow No. 5, HC Red No. 7, HC Blue No. 2, HC Yellow No. 4, HC Yellow No. 2, HC Orange No. 1, HC Red No. 1,2-Chloro-5-nitro-N-Hydroxyethyl-p-phenylenediamine, HC Red No. 3,4-Amino-3-nitrophenol, 2-Hydroxyethylamino-5-nitroanisole, 3-nitro-p-Hydroxyethylaminophenol, 2-amino-3-nitrophenol, 6-nitro-o-toluidine, 3-methylamino-4-nitrophenoxyethanol, 2-nitro-5-glycerymethylanaline, HC Yellow No. 11, HC Violet No. 1, HC Orange No. 2, HC Orange No. 3, HC Yellow No. 9, 4-Nitrophenyl Aminoethylurea, HC Red No. 10, HC Red No. 11,2-Hydroxyethyl picramic acid, HC Blue No. 12, HC Yellow No. 6, Hydroxyethyl-2-nitro-p-toluidine, HC Yellow No. 12, HC Blue No. 10, HC Yellow No. 7, HC Yellow No. 10, HC Blue No. 9, N-ethyl-3-nitro PABA, 4-amino-2-nitrophenyl-amine-2'-carboxylic acid, 2-chloro-6-ethylamino-4-nitrophenol, 6-Nitro-2,5-pyridinediamine, HC Violet No. 2, 2-amino-6-chloro-4-nitrophenol, 4-hydroxypropylamino-3-nitrophenol, HC Yellow No. 13, 1,2,3,4-Tetrahydro-6-nitrochinoxalin, HC Red No. 14, HC Yellow No. 15, HC Yellow No. 14, 3-Amino-6-methylamino-2-nitropyridine, 2,6-diamino-3-((pyridine-3-yl)azo)pyridine, Basic Red No. 118, Basic Orange No. 69, N-(2-nitro-4-aminophenyl)-allylamine, 4-[(4-Amino-3-methylphenyl)(4-Imino-3-methyl-2,5-Cyclohexadien-1-ylidene) Methyl]-2-Methyl-benzeneamine-Hydrochloride, 1H-Imidazolium,2-[[4-(dimethylamino)phenyl]azo]-1,3-dimethylchloride, Pyridinium, 1-methyl-4-[(methylphenyl-hydrazono)methyl]-, methyl sulfate, 1H-Imidazolium, 2-[(4-aminophenyl)azo]-1,3-dimethyl, chloride, Basic Red 22, Basic Red 76, Basic Brown 16, Basic Yellow 57, 7-(2',4'-Dimethyl-5'-sulfophenylazo)-5-sulfo-8-hydroxynaphthalene, Acid Orange 7, Acid Red 33, 1-(3'-Nitro-5'-sulfo-6'-oxophenylazo)-oxo-naphthalene chromium complex, Acid Yellow 23, Acid Blue 9, Basic Violet 14, Basic Blue 7, Basic Blue 26, Sodium salt of mixture of mono- & disulfonic acids (mainly the latter) of quinophthlanone or 2-quinolylindandione, Basic Red 2, Basic Blue 99, Disperse Red 15, Acid Violet 43, Disperse Violet 1, Acid Blue 62, Pigment Blue 15, Acid Black 132, Basic Yellow 29, Disperse Black 9, 1-(N-Methylmorpholinium-propylamino)-4-hydroxy-anthraquinone methylsulfate, HC Blue No. 8, HC Red No. 8, HC Green No. 1, HC Red No. 9, 2-Hydroxy-1,4-naphthoquinone, Acid Blue 199, Acid Blue 25, Acid Red 4,Henna Red, Indigo, Cochenille, HC Blue 14, Disperse Blue 23, Disperse Blue 3, Violet 2, Disperse Blue 377, Basic Red 51, Basic Orange 31, Basic Yellow 87, and mixtures thereof. Preferred direct dyes include but are not limited to: Disperse Black 9, HC Yellow 2, HC Yellow 4, HC Yellow 15, 4-nitro-o-phenylenediamine, 2-amino-6-chloro-4-nitrophenol, HC Red 3, Disperse Violet 1, HC Blue 2, Disperse Blue 3, Disperse Blue 377, Basic Red 51, Basic Orange 31, Basic Yellow 87, and mixtures thereof.

Oxidizing Agent

The compositions according to the present invention may comprise at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolourisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can also be used if desired. The oxidizing agents may be provided in aqueous solution or as a powder which is dissolved prior to use. Preferred for use in the compositions according to the present invention are hydrogen peroxide, percarbonate, persulphates and combinations thereof.

According to the present invention the compositions comprise from about 0.1% to about 15% by weight, preferably from about 1% to about 10% by weight, and most preferably from about 2% to about 7% by weight of an oxidizing agent.

Another preferred oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH of up to and including 9.5, preferably 7.5 to 9.5 more preferably about pH 9. Moreover, this system is also particularly effective in combination with a source of ammonia or ammonium ions. It has been found that this oxidizing agent can deliver improvements to the desired hair colour results particularly with regard to the delivery of high lift, whilst considerably reducing the odour, skin and scalp irritation and damage to the hair fibres.

Accordingly, any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate ions, carbamate and hydrocarbonate ions are sodium hydrogen carbonate, potassium hydrogen carbonate, ammonium carbamate, and mixtures thereof.

According to the present invention the compositions comprise from about 0.1% to about 15% by weight, preferably from about 1% to about 10% by weight, and most preferably from about 1% to about 8% by weight of a hydrogencarbonate ion and from about 0.1% to about 10% by weight, preferably from about 1% to about 7% by weight, and most preferably from about 2% to about 5% by weight of a source of hydrogen peroxide.

Thickeners

The inventive compositions may comprise a thickener in an amount sufficient to provide the composition with a viscosity so that it can be readily applied to the hair without unduly dripping off the hair and causing mess. Typically, such an amount will be at least 0.1%, preferably at least 0.5%, more preferably, at least 1%, by weight, of the hair dyeing and/or developer composition.

Preferred for use herein are salt tolerant thickeners, including but not limited to: xanthan, guar, hydroxypropyl guar, scleroglucan, methyl cellulose, ethyl cellulose (available as AQUACOTE™), hydroxyethyl cellulose (NATROSOL™), carboxymethyl cellulose, hydroxypropylmethyl cellulose, microcrystalline cellulose, hydroxybutylmethyl cellulose, hydroxypropyl cellulose (available as KLUCEL™), hydroxyethyl ethyl cellulose, cetyl hydroxyethyl cellulose (available as NATROSOL™ Plus 330), N-vinylpyrollidone (available as POVIDONE™), Acrylates/Ceteth-20 Itaconate Copolymer (available as STRUCTURE™ 3001), hydroxypropyl starch phosphate (available as STRUCTURE™ ZEA), polyethoxylated urethanes or polycarbamyl polyglycol ester (e.g. PEG-150/Decyl/SMDI copolymer (available as ACULYN™ 44), PEG-150/Stearyl/SMDI copolymer available as ACULYN™ 46), trihydroxystearin (available as THIXCIN™), acrylates copolymer (e.g. available as ACULYN™ 33) or hydrophobically modified acrylate copolymers (e.g. Acrylates/Steareth-20 Methacrylate Copolymer (available as ACULYN™ 22), non-ionic amphophilic polymers comprising at least one fatty chain and at least one hydrophilic unit selected from polyether urethanes comprising at least one fatty chain, and blends of Ceteth—10 phosphate, Di-cetyl phosphate and Cetearyl alcohol (available as CRODAFOS™ CES).

Chelants

The inventive compositions may comprise chelants in an amount sufficient to reduce the amount of metals available to interact with formulation components, particularly oxidizing agents, more particularly peroxides. Typically such an amount will range from at least 0.25%, preferably at least 0.5%, by weight, of the composition. Suitable chelants for use herein include but are not limited to: diamine-N,N'-dipolyacid, monoamine monoamide-N,N'-dipolyacid, and N,N'-bis(2-hydroxybenzyl)ethylenediamine-N,N'-diacetic acid chelants (preferably EDDS (ethylenediaminedisuccinic acid)), carboxylic acids (preferably aminocarboxylic acids), phosphonic acids (preferably aminophosphonic acids) and polyphosphoric acids (in particular straight polyphosphoric acids), their salts and derivatives.

pH Modifiers and Buffering Agents

The inventive compositions may further comprise a pH modifier and/or buffering agent in an amount that is sufficiently effective to adjust the pH of the composition to fall within a range from 3 to 13, preferably from 8 to 12, more preferably from 9 to 11. Suitable pH modifiers and/or buffering agents for use herein include, but are not limited to: ammonia, alkanolamides such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, preferably sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

Alkalising Agent

According to the present invention the composition may optionally comprise at least one source of alkalizing agent, preferably a source of ammonium ions and or ammonia. Any agent known in the art may be used such as alkanolamides for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol and guanidium salts. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonium hydrogen carbonate, ammonia and mixtures thereof. The compositions of the present invention may comprise from about 0.1% to about 10% by weight, preferably from about 0.5% to about 5%, most preferably from about 1% to about 3% of an alkalizing agent, preferably ammonium ions.

Radical Scavenger

According to the present invention the compositions may further comprise a source of radical scavenger. As used herein the term radical scavenger refers to a species that can react with a reactive radical, preferably carbonate radicals, to convert the reactive radical by a series of fast reactions to a less reactive species.

Suitable radical scavengers for use herein include compounds according to the general formula:

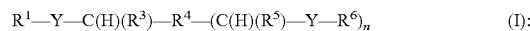

$$R^1-Y-C(H)(R^3)-R^4-(C(H)(R^5)-Y-R^6)_n \quad \text{(I)}:$$

wherein Y is $NR^2$, O, or S, preferably $NR^2$, n is 0 to 2, and wherein $R^4$ is monovalent or divalent and is selected from: (a) substituted or unsubstituted, straight or branched, alkyl, mono- or poly-unsaturated alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; the systems of (a), (b) and (c) comprising from 1 to 12 carbon atoms and 0 to 5 heteroatoms selected from O, S, N, P, and Si; and wherein $R^4$ can be connected to $R^3$ or R to create a 5, 6 or 7 membered ring; and wherein $R^1$, $R^2$, $R^3$, $R^5$, and $R^6$ are monovalent and are selected independently from: (a), (b) and (c) described herein above, or H.

Preferably, $R^4$ is selected from: (a) substituted or unsubstituted, straight or branched, alkyl, heteroalkyl, aliphatic, heteroaliphatic, or heteroolefinic systems, (b) substituted or unsubstituted, mono- or poly-cyclic aliphatic, aryl, or heterocyclic systems, or. (c) substituted or unsubstituted, mono-, poly-, or per-fluoro alkyl systems; more preferably $R^4$ is selected from (a) substituted or unsubstituted, straight or branched, alkyl, heteroalkyl, aliphatic, or heteroaliphatic systems, (b) substituted or unsubstituted, aryl, or heterocyclic systems, or (c) substituted or unsubstituted, mono-, poly-, or per-fluoro alkyl systems; more preferably substituted or unsubstituted, straight or branched, alkyl, or heteroalkyl systems.

Preferably, the $R^4$ systems of (a), (b), and (c), described herein above, comprise from 1 to 8 carbon atoms, preferably from 1 to 6, more preferably from 1 to 4 carbon atoms and from 0 to 3 heteroatoms; preferably from 0 to 2 heteroatoms; most preferably from 0 to 1 heteroatoms. Where the systems contain heteroatoms, preferably they contain 1 heteroatom. Preferred heteroatoms include O, S, and N; more preferred are O, and N; and most preferred is O.

Preferably, $R^1$, $R^2$, $R^3$, $R^5$, and $R^6$ are selected independently from any of the systems defined for $R^4$ above, and H.

In alternative embodiments, any of $R^1$, $R^2$, $R^3$, $R^4$, $R^5$, and $R^6$ groups are substituted. Preferably, the substituent(s) is selected from: (a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) comprising from 1 to 10 carbon atoms and 0 to 5 heteroatoms selected from O, S, N, P, and Si; (b) the group of S-linked monovalent substituents consisting of $SA^1$, SCN, $SO_2A^1$, $SO_3A^1$, $SSA^1$, $SOA^1$, $SO_2NA^1A^2$, $SNA^1A^2$, and $SONA^1A^2$; (c) the group of O-linked monovalent substituents consisting of $OA^1$, OCN and $ONA^1A^2$; (d) the group of N-linked monovalent substituents consisting of $NA^1A^2$, $(NA^1A^2A^3)^+$, NC, $NA^1OA^2$, $NA^1SA^2$, NCO, NCS, $NO_2$, $N=NA^1$, $N=NOA^1$, $NA^1CN$, $NA^1NA^2A^3$; (e) the group of monovalent substituents consisting of $COOA^1$, $CON_3$, $CONA^1_2$, $CONA^1COA^2$, $C(=NA^1)NA^1A^2$, CHO, CHS, CN, NC, and X; and (f) the group consisting fluoroalkyl monovalent substituents consisting of mono-, poly-, or per-fluoro alkyl systems comprising from 1 to 12 carbon atoms and 0 to 4 heteroatoms.

For the groups (b) to (e), described above, $A^1$, $A^2$, and $A^3$ are monovalent and are independently selected from: (1) H, (2) substituted or unsubstituted, straight or branched, alkyl, mono- or poly-unsaturated alkyl, heteroalkyl, aliphatic, heteroaliphatic, or heteroolefinic systems, (3) substituted or unsubstituted, mono- or poly-cyclic aliphatic, aryl, or heterocyclic systems, or (4) substituted or unsubstituted, mono-, poly-, or per-fluoro alkyl systems; said systems of (2), (3) and (4) comprising from 1 to 10 carbon atoms and 0 to 5 heteroatoms selected from O, S, N, P, and Si; and wherein X is a halogen selected from the group consisting of F, Cl, Br, and I.

Preferred substituents for use herein include those having a Hammett Sigma Para ($\sigma_p$) Value from −0.65 to +0.75, preferably from −0.4 to +0.5. Hammett Sigma Values are described in Advanced Organic Chemistry—Reactions, Mechanisms and Structure (Jerry March, $5^{th}$ ed. (2001) at pages 368-375).

Alternative suitable radical scavengers for use herein are compounds according to the general formula (II):

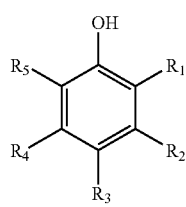

(II)

wherein $R_1$, $R_2$, $R_3$, $R_4$, and $R_5$ are each independently selected from H, $COO^-M^+$, Cl, Br, $SO_3^-M^+$, $NO_2$, $OCH_3$, OH or a $C^1$ to $C^{10}$ primary or secondary alkyl and M is either H or alkali metal. Preferably, the above-described radical scavengers have a pKa of more than 8.5 to ensure protonation of the hydroxy group.

Other suitable radical scavengers for use herein include those selected from group (III) benzylamine, imidazole, di-tert-butylhydroxytoluene, hydroquinone, guanine, pyrazine, piperidine, morpholine, methylmorpholine, 2methyoxyethylamine, and mixtures thereof.

Preferred radical scavengers according to the present invention are selected from the classes of alkanolamines, amino sugars, amino acids, esters of amino acids and mixtures thereof. Particularly preferred compounds are: monoethanolamine, 3-amino-l-propanol, 4-amino-1-butanol,5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof. Especially preferred compounds are glycine, sarcosine, lysine, serine, 2 methoxyethylamine, glucosamine, glutamic acid, morpholine, piperdine, ethylamine, 3 amino-1-propanol and mixtures thereof.

The radical scavengers according to the present invention preferably have a molecular weight of less than about 500, preferably less than about 300, more preferably less than about 250 in order to facilitate penetration of the radical scavenger into the hair fibre. The compositions of the present invention preferably comprise from about 0.1% to about 10% by weight, preferably from about 1% to about 7% by weight of radical scavenger. The radical scavenger is also preferably selected such that it is not an identical species as the alkalizing agent. According to one embodiment of the present invention the radical scavenger may be formed insitu in the hair dyeing compositions prior to application to the hair fibres.

Conditioning Agents

The compositions of the present invention may comprise or are used in combination with a composition comprising a conditioning agent. Conditioning agents suitable for use herein are selected from silicone materials, amino silicones, fatty alcohols, polymeric resins, polyol carboxylic acid esters, cationic polymers, cationic surfactants, insoluble oils and oil derived materials and mixtures thereof. Additional materials include mineral oils and other oils such as glycerin and sorbitol.

The conditioning agent will generally be used at levels of from about 0.05% to about 20% by weight of the hair dyeing product composition, preferably of from about 0.1% to about 15%, more preferably of from about 0.2% to about 10%, even more preferably of from about 0.2% to about 2%.

Particularly useful conditioning materials are cationic polymers. Conditioners of cationic polymer type may be chosen from those already known by those skilled in the art as improving at least one cosmetic properties of keratin fibres treated with a cosmetic composition. Cationic polymers can be chosen from those comprising units of at least one amine group chosen from primary, secondary, tertiary and quaternary amine groups that may either form part of the main polymer chain, or be borne by a side substituent that is directly attached to the main polymer chain. Such cationic polymers generally have a number average molecular mass ranging from 500 to $5 \times 10^6$, or more preferably from 1000 to $3 \times 10^6$.

III. Methods of Manufacture

The compounds of this invention may be obtained using conventional methods. A general description of how to make the compounds is provided above and specific examples are provided below. The compositions of this invention may also be obtained using conventional methods. The hair dyeing compositions may be formed as solutions, preferably as aqueous or aqueous-alcohol solutions. The hair dye product compositions may preferably be formed as thick liquids, creams, gels, or emulsions whose composition is a mixture of the dye compound and other dye ingredients with conventional cosmetic additive ingredients suitable for the particular preparation and preferably with the developer composition.

IV. Methods of Use

The inventive hair dyeing compositions may be used by admixing them with a suitable oxidant, which reacts with the oxidative dye precursors to develop the hair dye product composition. The oxidant is usually provided in an aqueous composition, i.e. developer composition, which normally is provided as a separate component of the finished hair dyeing product system and present in a separate container. The developer composition may also contain, to the extent compatible, various ingredients needed to form the developer composition, e.g. peroxide stabilizers, foam formers, etc., and may incorporate one or more of the adjuvants referred to above. Upon mixing the hair dyeing composition and the developer composition to form a hair dye product composition, the adjuvants are provided in the hair dye product composition as it is applied to the hair to achieve desired product attributes, e.g., pH, viscosity, rheology, etc.

The hair dyeing product composition as it is applied to the hair, can be weakly acidic, neutral or alkaline according to their composition, typically having a pH from 6 to 11, preferably from 7 to 10, more preferably from 8 to 10. The pH of the developer composition is typically acidic, and generally the pH is from 2.5 to 6.5, preferably from 3 to 5. The pH of the hair dye and developer compositions may be adjusted using a pH modifier as mentioned above.

In order to use the hair dyeing product composition, the above-described compositions are mixed immediately prior to use and a sufficient amount of the mixture is applied to the hair, according to the hair abundance, generally from 60 to 200 grams. Upon such preparation the hair dye product composition is applied to the hair to be dyed and remains in contact with the hair for an amount of time effective to dye the hair. Typically, the hair dye product composition is allowed to act on the hair for 2 to 60, preferably 15 to 45, more preferably, 30 minutes, at a temperature ranging from 15° C. to 50° C. Thereafter, the hair is rinsed with water, to remove the hair dye product composition and dried. If necessary, the hair is washed with a shampoo and rinsed, e.g., with water or a weakly acidic solution, such as a citric acid or tartaric acid solution, and dried. Optionally, a separate conditioning product may also be provided.

Together, the hair dyeing composition and the developer composition form a system for dyeing hair. This system may be provided as a kit comprising in a single package separate containers of the hair dyeing composition, the developer composition, the optional conditioner or other hair treatment product, and instructions for use.

EXAMPLES

Example 1

Synthesis of 2-amino-3,5,6 trimethyl phenol

This example shows the synthesis route for a preferred compound of the invention, which is suitable for use in the compositions of the invention:

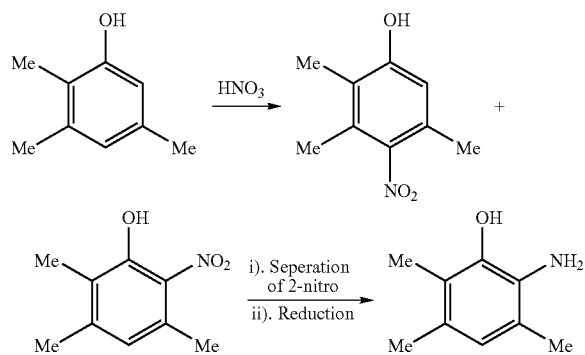

The Lab values of this compound verses reference compounds (2-amino phenol and 5-methyl 2-aminophenol) below clearly illustrate that this compound provides at least equivalent performance with regard to delivery of yellow colour. The following performance data was generated by dyeing out 0.02M concentration of the dye precursor from the exemplified hair dyeing product compositions below. The hair dyeing product composition was applied at a dosage of four grams of product per gram of hair. The hair switch was then placed in an oven at 30° C. for 30 minutes, after which time the hair switch was rinsed in warm tap water until the resulting water ran clear and was then left to dry. Once dry, the colour of the switch was measured on a Minolta 1600D Spectrophotometer.

| Compound (all 0.02M) | L | A | b |
|---|---|---|---|
| 2-aminophenol (reference) | 68.4 | 5.62 | 38.7 |
| 5-methyl 2-aminophenol (reference) | 76.0 | 1.02 | 57.23 |
| 3,5,6 trimethyl 2-aminophenol | 77.2 | −8.8 | 51.2 |

TABLE 1

Examples 1 to 10, which illustrate the inventive hair dyeing compositions, may be formulated as thickened, aqueous solutions, by conventional methods. A suitable procedure is described below.

| Ingredient | 1 | 2 | 3 | 4 | 5 | 6 | 7 | 8 | 9 | 10 |
|---|---|---|---|---|---|---|---|---|---|---|
| Sodium Sulphite | — | — | 0.1 | 0.1 | 0.1 | 0.1 | 0.1 | 0.3 | 0.1 | — |
| Ascorbic Acid | 0.5 | 0.1 | — | 0.1 | 0.3 | — | 0.6 | 0.1 | 0.1 | 0.2 |
| Ammonium Hydroxide | 6 | 8 | 8 | 7 | 8 | 9 | 10 | 8 | 8 | 10 |
| Ethylenediamedisuccinic acid | — | — | — | 1 | — | 1 | — | 0.5 | — | 1.5 |
| Oleth 5 | 1 | 2 | 3 | 0.5 | 1 | 1.5 | — | 0.8 | 2 | 1 |
| Oleth 2 | 0.8 | — | 0.8 | 0.8 | 1.5 | 2 | 0.8 | 0.5 | 0.8 | 2.5 |
| Oleic Acid | 0.9 | 1 | — | 0.3 | — | 0.9 | 0.9 | 0.8 | 1.1 | 0.9 |
| Soytrimonium chloride | 7 | 6 | 6 | 7 | 7 | — | — | 8 | 5 | 7 |
| Cocamide DEA | 3 | 1 | 1 | 3 | 0.5 | 0.8 | — | — | 3 | 2 |
| EDTA (Na₄ salt) | 0.1 | 0.1 | 0.1 | 0.1 | 0.1 | — | 0.1 | 0.1 | 0.1 | 0.1 |
| 1,4 diaminobenzene | 0.8 | 0.5 | — | 0.5 | 0.8 | — | 0.5 | 0.6 | 0.5 | 0.8 |
| 4-aminophenol | 0.2 | — | — | 0.1 | 0.2 | — | — | 0.2 | 0.1 | 0.2 |
| 3-aminophenol | 0.5 | 0.5 | — | 0.6 | 1 | — | 0.5 | 1 | 0.6 | 1 |
| 4-amino-3-methylphenol | 0.2 | — | — | 0.2 | 0.2 | — | 1 | — | 0.2 | 0.3 |
| 2-(4,5-diamino-1H-pyrazol-1-yl)ethanol | — | 0.5 | — | — | 0.5 | — | 0.5 | 1 | — | 0.3 |
| N,N-Bis(2-hydroxyethyl)-p-phenylenediamine | — | 0.4 | — | 1 | 0.2 | — | 0.2 | — | 0.2 | 0.3 |
| 2-aminophenol | 1 | 1 | — | — | — | — | — | — | — | — |
| 3,5,6-trimethyl-2-aminophenol | — | — | — | 1 | — | — | — | — | — | — |
| 3,5,6-trimethoxymethyl 2-aminophenol | 1 | 0.5 | — | — | 1 | 1.5 | 1 | — | — | — |
| 3,5,6-triethyl 2-aminophenol | — | — | 1 | 0.8 | — | — | — | 1 | 1 | 1 |
| Propylene Glycol | 8.2 | 8 | 7.8 | 8.2 | 8.4 | 8 | 8.2 | 8.2 | 7.8 | 8.2 |
| Hexylene Glycol | 8 | 7 | 8 | 6 | 8 | 8 | — | 9 | 8 | 9 |
| Ethoxy Diglycol | 4.2 | 4 | 4.6 | 4.2 | 4.2 | 5 | 4.2 | 3 | 4.2 | 4.2 |
| Water | qs | qs | qs | qs | qs | qs | qs | qs | qs | qs |

To prepare pre-mix: Add to a suitable vessel in the following order, citric acid, ethoxy diglycol, oleic acid, propylene glycol, and cocaamidopropyl betaine, then agitate until fully dispersed, then add Oleth-10, Oleth-2 and acrylate co-polymers, continue the agitation for 10 minutes and transfer to main vessel. To the main vessel then add water (heated to 50° C.), oleic acid, water, sodium sulphite, and EDTA. Next weigh out and add the ascorbic acid, then stir well until dissolved. Separately weigh dyes into a clean beaker and transfer also to the main vessel. Add the dyes and stir until dissolved (heat to 40° C. as necessary). Cool to room temperature with stirring, add the ammonium hydroxide and water with stirring, add citric acid to pH 10, and transfer to the storage container.

TABLE 2

Examples 11 to 20, which illustrate the inventive hair dyeing compositions, may be formulated as emulsions, by conventional methods. The procedure described for Examples 3 to 12 is suitable.

| Ingredient | Composition Example Number | | | | | | | | | |
|---|---|---|---|---|---|---|---|---|---|---|
|  | 11 | 12 | 13 | 14 | 15 | 16 | 17 | 18 | 19 | 20 |
| Sodium Sulphite | — | — | 0.1 | 0.1 | 0.1 | 0.1 | 0.1 | 0.3 | 0.1 | — |
| Ascorbic Acid | 0.5 | 0.1 | — | 0.1 | 0.3 | — | 0.6 | 0.1 | 0.1 | 0.2 |
| Ammonium Carbonate | 3 | 6 | 2 | — | 4 | 8 | 2 | — | 4 | 6 |
| Potassium Hydrogen Carbonate | — | — | 1.5 | 2 | — | — | 2 | 2 | — | — |
| Ammonium Acetate | — | — | — | 2 | — | — | — | 2 | — | — |
| Ceteareth 25 | 1 | — | 1.5 | 1 | 1 | 2 | 1 | 1 | — | 1 |
| Cetyl Alcohol | 1.6 | 1.2 | 1.6 | 1.6 | — | 1.8 | 1.6 | 1.6 | 2 | 1.6 |
| Stearyl Alcohol | 3.3 | — | 3.3 | 3 | 3.3 | 2.5 | 3.3 | 4 | 3.3 | — |
| Sodium Benzoate | 0.1 | 0.1 | 0.1 | 0.1 | 0.1 | 0.1 | 0.1 | 0.1 | 0.1 | 0.1 |
| Phenoxyethanol | 0.1 | 0.1 | 0.1 | 0.1 | 0.1 | 0.1 | 0.1 | 0.1 | 0.1 | 0.1 |
| EDTA (Na$_4$ salt) | 0.1 | 0.1 | 0.1 | 0.1 | 0.1 | 0.1 | 0.1 | 0.1 | 0.1 | 0.1 |
| Sodium Glycinate | 2 | 5 | 3 | 1 | — | — | — | — | — | 3 |
| Glutamic Acid | — | — | — | 2 | 2 | 6 | 2 | — | — | — |
| Glucosamine | — | — | — | — | — | — | 2 | 4 | 4 | 3 |
| 1,4 diaminobenzene | 0.8 | 0.5 | 0.6 | — | 0.8 | 0.8 | 0.5 | 0.6 | — | 0.8 |
| 4-aminophenol | 0.2 | 0.3 | 0.2 | — | 0.2 | 0.2 | 0.3 | 0.2 | — | 0.2 |
| 3-aminophenol | 1 | — | 0.5 | 1 | — | 1 | 1 | 0.5 | 1 | — |
| 1,3 dihydroxybenzene | 1.6 | 1.2 | 1.6 | — | 1.6 | 1.6 | 1.2 | 1.6 | — | 1.6 |
| 4-amino-3-methylphenol | 0.2 | — | — | 0.2 | 0.2 | — | 1 | — | 0.2 | 0.3 |
| 2-(4,5-diamino-1H-pyrazol-1-yl)ethanol | — | 0.5 | — | — | 0.5 | — | 0.5 | 1 | — | 0.3 |
| N,N-Bis(2-hydroxyethyl)-p-phenylenediamine | — | 0.4 | — | 1 | 0.2 | — | 0.2 | — | 0.2 | 0.3 |
| 2-aminophenol | 1 | 1 | — | — | — | — | — | — | — | — |
| 3,5,6-trimethyl-2-aminophenol | — | — | 1 | 1 | — | — | — | — | — | — |
| 3,5,6-trimethoxymethyl 2-aminophenol | 1 | 1 | 1 | 1 | 1 | 1 | 1 | — | — | — |
| 3,5,6-triethyl 2-aminophenol | — | 1 | 1 | — | — | — | — | 1 | 1 | 1 |
| pH adjust to pH 9.0 | qs | qs | qs | qs | qs | qs | qs | qs | qs | qs |
| Water | qs | qs | qs | qs | qs | qs | qs | qs | qs | qs |

TABLE 3

Examples 21 to 30, which illustrate the inventive hair dyeing compositions, may be formulated as emulsions, by conventional methods. The procedure described for Examples 3 to 12 is suitable.

| Ingredient | Composition Example Number | | | | | | | | | |
|---|---|---|---|---|---|---|---|---|---|---|
|  | 21 | 22 | 23 | 24 | 25 | 26 | 27 | 28 | 29 | 30 |
| Sodium Sulphite | — | — | 0.1 | 0.1 | 0.1 | 0.1 | 0.1 | 0.3 | 0.1 | — |
| Ascorbic Acid | 0.5 | 0.1 | — | 0.1 | 0.3 | — | 0.6 | 0.1 | 0.1 | 0.2 |
| Ammonium Carbonate | 3 | 6 | 2 | — | 4 | 8 | 2 | — | 4 | 6 |
| Potassium Hydrogen Carbonate | — | — | 1.5 | 2 | — | — | 2 | 2 | — | — |
| Ammonium Acetate | — | — | — | 2 | — | — | — | 2 | — | — |
| Blended phosphate thickener[1] | 3 | 2 | 1.5 | 4 | 3 | 1 | 1.8 | 2 | 3 | 3 |
| EDTA (Na$_4$ salt) | 0.1 | 0.1 | 0.1 | 0.1 | 0.1 | 0.1 | 0.1 | 0.1 | 0.1 | 0.1 |
| Sodium Glycinate | 2 | 5 | 3 | 1 | — | — | — | — | — | 3 |
| Glutamic Acid | — | — | — | 2 | 2 | 6 | 2 | — | — | — |
| Glucosamine | — | — | — | — | — | — | 2 | 4 | 4 | 3 |
| 1,4 diaminobenzene | 0.8 | — | 0.6 | 0.5 | 0.8 | 0.8 | 0.5 | 0.6 | — | 0.8 |
| 4-aminophenol | 0.2 | — | 0.2 | 0.1 | 0.2 | 0.2 | 0.3 | 0.2 | — | 0.2 |
| 3-aminophenol | 1 | — | 1 | 0.6 | 1 | 1 | 0.5 | 1 | — | 1 |
| 1,3 dihydroxybenzene | 1.6 | — | 1.6 | 0.8 | 1.6 | 1.6 | 1.2 | 1.6 | — | 1.6 |
| 4-amino-3-methylphenol | 0.2 | — | — | 0.2 | 0.2 | — | 1 | — | 0.2 | 0.3 |
| 2-(4,5-diamino-1H-pyrazol-1-yl)ethanol | — | 0.5 | — | — | 0.5 | — | 0.5 | 1 | — | 0.3 |
| N,N-Bis(2-hydroxyethyl)-p-phenylenediamine | — | 0.4 | — | 1 | 0.2 | — | 0.2 | — | 0.2 | 0.3 |
| 2-aminophenol | 1 | — | — | — | — | — | — | — | — | — |
| 3,5,6-trimethyl-2-aminophenol | — | — | 1 | 1 | — | — | — | — | — | — |
| 3,5,6-trimethoxymethyl 2-aminophenol | 1 | 1 | — | — | 1 | 1 | 1 | — | — | — |
| 3,5,6-triethyl 2-aminophenol | — | — | 1 | 1 | — | — | — | 1 | 1 | 1 |
| pH adjust to pH 9.0 | qs | qs | qs | qs | qs | qs | qs | qs | qs | qs |
| Water | qs | qs | qs | qs | qs | qs | qs | qs | qs | qs |

[1]Ceteth-10 phosphate/di-cetyl phosphate/cetearyl alcohol blend, available as CRODAFOS (TM) CES, from Croda (United Kingdom).

TABLE 4

Example 31 illustrates developer compositions which may be used with the hair dyeing example formulations number 1-30 and may be formulated by conventional methods described below.

| Ingredient | Composition Example Number 31 % Weight |
|---|---|
| Oleyl Alcohol | 0.1-2.0 |
| Steareth-21 | 1.0-5.0 |
| Acrylates Copolymer | 1.0-10.0 |
| PEG-50 | 0.1-2.0 |
| Water | 50.0-90.0 |
| Hydrogen Peroxide - 50% | 10.0-15.0 |
| Acrylates/Steareth-20 Methacrylate copolymer | 0.1-2.0 |
| Oleth-2 | 0.1-2.0 |
| Oleth-5 | 0.1-2.0 |
| Etidronic Acid | 0.01-0.1 |
| Disodium EDTA | 0.01-0.1 |
| Simethicone | 0.001-0.01 |

To prepare:—All vessels should first be passivated as follows: Fill vessel to about 10% full with concentrated hydrogen peroxide and then fill to the top with deionized water (DI). Add plastic overhead stirrer, plastic spatulas and glass thermometer that will be used in process. Swirl to mix; pour solution out, rinse with DI water, fill with fresh peroxide solution; add stirrer and spatulas. Cover with plastic film/cover; allow to stand for 24 hours, pour out and dry. Once done add 60% water to a tared vessel, heat to 70-75° C. and maintain this temperature. Add the steareth-21 and stir until dissolved. Whilst stirring pre-melt the PEG-50 on a hot plate and when the steareth has dissolved add to the batch. Then add each of the following ingredients one at a time, waiting for each to dissolve before adding the next; Oleth-2, Oleth-5, Oleyl Alcohol, EDTA and Etidronic acid. Mix the batch for 15minutes. Remove from the heat and add the remaining water, then allow the batch to cool to 35° C. Add the hydrogen peroxide, followed by the remaining ingredients. Finally retare the vessel and q.s. with water. Product can be stored in storage containers (no metal caps) for up to 6 months.

The exemplified hair dyeing compositions are typically pre-mixed in a 1:1 ratio with the developer composition prior to application onto the keratinous fibres.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition for the oxidative dyeing of keratin fibres, comprising a medium suitable for dyeing and from about 0.001% to about 10% by weight of the composition of a compound of the formula (I), or its salts with an inorganic or organic acid,

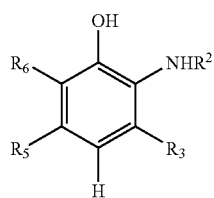

(I)

wherein $R^3$, $R^5$ and $R^6$ are substituted and are independently selected from:
(a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, and (iii) substituted or unsubstituted, mono-, poly-, or per-fluoro alkyl systems; said systems of (i), (ii) and (iii) independently comprising from about 1 to about 10 carbon atoms and from about 0 to about 5 heteroatoms independently selected from O, S, N, P, and Si;
(b) the group of S-linked substituents consisting of $SA^{16}$, SCN, $SO_2A^{16}$, $SO_3A^{16}$, $SSA^{16}$, $SOA^{16}$, $SO_2NA^{16}A^{17}$, $SNA^{16}A^{17}$, and $SONA^{16}A^{17}$;
(c) the group of O-linked substituents consisting of $OA^{16}$, OCN and $ONA^{16}A^{17}$;
(d) the group of N-linked substituents consisting of $NA^{16}A^{20}$, $(NA^{16}A^{17}A^{18})^+$, NC, $NA^{16}OA^{17}$, $NA^{16}SA^{17}$, NCO, NCS, N=$NA^{16}$, N=$NOA^{16}$, $NA^{16}CN$, and $NA^{16}NA^{17}A^{18}$;
(e) the group of substituents consisting of $COOA^{19}$, $CON_3$, $CONA^{16}{}_2$, $CONA^{16}COA^{17}$, C(=$NA^{16}$)$NA^{16}A^{17}$, CHO, CHS, CN, NC, and X; and
(f) the group of fluoroalkyl substituents consisting of mono-, poly-, and per-fluoro alkyl systems comprising from about 1 to about 12 carbon atoms and from about 0 to about 4 heteroatoms, wherein, $A^{16}$, $A^{17}$, and $A^{18}$ are monovalent and are independently selected from:
(1) H,
(2) substituted or unsubstituted, straight or branched, alkyl, mono- or poly-unsaturated alkyl, heteroalkyl, aliphatic, heteroaliphatic, or heteroolefinic systems,
(3) substituted or unsubstituted, mono- or poly-cyclic aliphatic, aryl, or heterocyclic systems, and
(4) substituted or unsubstituted, mono-, poly-, or per-fluoro alkyl systems; said systems of (2), (3) and (4) comprising independently from about 1 to about 10 carbon atoms and from about 0 to about 5 heteroatoms independently selected from O, S, N, P, and Si; and wherein X is a halogen selected from the group consisting of F, Cl, Br, and I, and wherein $A^{19}$ is monovalent and independently selected from
(1) substituted or unsubstituted, straight or branched, alkyl, mono- or poly-unsaturated alkyl, heteroalkyl, aliphatic, heteroaliphatic or heteroolefinic systems,
(2) substituted or unsubstituted, mono or poly-cyclic aliphatic, aryl, or heterocyclic systems, and
(3) substituted or unsubstituted, mono-, poly- or per-fluoro alkyl systems; said systems of (2) and (3) comprising independently from about 2 to about 10 carbon atoms and from about 0 to about 5 heteroatoms independently selected from O, S, N, P and Si, and wherein X is a halogen selected from the group consisting of F, Cl, Br and I and $A^{20}$ is monovalent and is independently selected from:
(1) substituted or unsubstituted, straight or branched, alkyl, mono- or poly-unsaturated alkyl, heteroalkyl, aliphatic, heteroaliphatic, or heteroolefinic systems,
(2) substituted or unsubstituted, mono- or poly-cyclic aliphatic, aryl, or heterocyclic systems, and
(3) substituted or unsubstituted, mono-, poly-, or per-fluoro alkyl systems; said systems of (1), (2) and (3) independently comprising from about 1 to about 10 carbon atoms and from about 0 to about 5 heteroatoms independently selected from O, S, N, P, and Si; and wherein X is a halogen selected from the group consisting of F, Cl, Br, and I and wherein $R^2$ is selected from any of the groups (a), (b), (c), (d), (e) and (f) and H.

2. A composition according to claim 1, further comprising a primary intermediate selected from p-phenylenediamine, p-aminophenol, o-phenylenediamine, o-aminophenol, heterocyclics, derivatives thereof, and mixtures thereof.

3. A composition according to claim 1, further comprising a coupler selected from phenol, resorcinol, naphthol, m-phenylenediamine, m-aminophenol, heterocyclics, derivatives thereof, and mixtures thereof.

4. A composition according to claim 1, further comprising a primary intermediate and coupler combination selected from the group consisting of: (a) resorcinol, 4-amino-m-cresol, 2-methylresorcinol, 4-amino-2-hydroxytoluene, m-aminophenol and 2-amino-4-hydroxyethyl anisole sulphate; (b) resorcinol, 4-amino-m-cresol, 2-methylresorcinol, 4-amino-2-hydroxytoluene, m-aminophenol, 2-amino-4-hydroxyethyl anisole sulphate, 1-napthol and toluene-2,5-diamine; (c) 2-methyl-5-hydroxyethylaminophenol, resorcinol, toluene-2,5 -diamine, m-aminophenol, p-aminophenol and p-methylaminophenol; (d) 2-methyl-5-hydroxyethylaminophenol, m-aminophenol, p-aminophenol, p-methylaminophenol and p-phenylenediamine; (e) 1-hydroxyethyl-4,5-diamino pyrazole sulphate and m-aminophenol; and (f) 2-methylresorcinol, p-aminophenol, 4-amino-2-hydroxytoluene, p-phenylenediamine and N,N-Bis(2-hydroxyethyl)-p-phenylenediamine.

5. A composition according to claim 1, further comprising an oxidizing agent selected from the group consisting of: hydrogen peroxide; inorganic alkali metal peroxides; organic peroxides; inorganic perhydrate salt bleaching compounds; alkali metal bromates; enzymes; and mixtures thereof.

6. A composition according to claim 1, further comprising a thickener selected from the group consisting of: xanthan, guar, hydroxypropyl guar, ethyl cellulose, hydroxyethyl cellulose, hydroxypropyl cellulose, N-vinylpyrollidone, Acrylates/Ceteth-20 Itaconate copolymer, PEG-150/Decyl/SMDI copolymer, PEG-1 50/Stearyl/SMDI copolymer, trihydroxystearin, Acrylates/Steareth-20 Methacrylate copolymer, blended Ceteth-10 phosphate/Di-cetyl phosphate/Cetearyl alcohol, and mixtures thereof.

7. A composition according to claim 1, further comprising a chelant.

8. A composition according to claim 1, wherein said medium comprises a solvent selected from the group consisting of water, ethanol, propanol, isopropanol, glycerol, 1,2-propylene glycol, hexylene glycol, ethoxy diglycol, and mixtures thereof.

9. A method for oxidative dyeing of keratin fibres, said method comprising the step of applying a composition according to claim 1 to keratin fibres in the presence of an oxidizing agent.

10. A multi-compartment device for the oxidative dyeing of keratin fibres or a multi-compartment kit for the oxidative dyeing of keratin fibres, comprising at least a first compartment containing a composition according to claim 1, and at least a second compartment containing an oxidizing composition.

* * * * *